United States Patent [19]

Pu

[11] Patent Number: 6,034,377
[45] Date of Patent: Mar. 7, 2000

[54] CHARGED PARTICLE BEAM IRRADIATION APPARATUS AND METHOD OF IRRADIATION WITH CHARGED PARTICLE BEAM

[75] Inventor: Yuehu Pu, Tokyo, Japan

[73] Assignee: Mitsubishi Denki Kabushiki Kaisha, Tokyo, Japan

[21] Appl. No.: 09/069,944

[22] Filed: Apr. 30, 1998

[30] Foreign Application Priority Data

Nov. 12, 1997 [JP] Japan ................................. 9-310433

[51] Int. Cl.[7] ..................................................... A61N 5/00
[52] U.S. Cl. ....................................... 250/492.3; 250/398
[58] Field of Search ............................... 250/492.3, 398; 378/137, 65

[56] References Cited

U.S. PATENT DOCUMENTS 3,903,421  9/1975  Benedetti ............................... 250/398
5,267,294  11/1993  Kuroda et al. ........................ 250/492.3

OTHER PUBLICATIONS

Pedroni et al.; "The 200–MeV proton therapy project at the Paul Scherrer Institute: Conceptual design and practical realization" Med. Phys. 22(1), pp. 37–53, Jan. 1995.

Chu et al.; "Instrumentation for treatment of cancer using proton and light–ion beams", Rev. Sci. Instrum. 64 (8), pp. 2055–2123, Aug. 1993.

Jongen et al.; "Development of a Low–Cost Compact Cyclotron System For Proton Therapy", Proceedings of the NIRS Intl. Workshop, Nat. Inst. of Radiological Sciences, pp. 189–200, Jul. 4–5, 1991.

*Primary Examiner*—Jack Berman
*Attorney, Agent, or Firm*—Leydig, Voit & Mayer, Ltd.

[57] ABSTRACT

A charged particle beam irradiation apparatus includes two electromagnets arranged in series along a direction of an incident axis of a charged particle beam, for deflecting the charged particle beam in opposite directions, an energy modulator including a cylindrical member having a length and a distribution of wall thickness in a circumferential direction, a first rotational drive for rotating the cylindrical member around a rotation axis, and a detector for detecting the angular position of the cylindrical member. The energy modulator is disposed at a downstream side of the scanning electromagnets so that the deflected charged particle beam passes through the rotation axis. The apparatus includes an energy degrader for limiting energy of the charged particle beam, and a second rotational drive for rotating the scanning electromagnets and the energy modulator together around the incident axis of the charged particle beam.

7 Claims, 10 Drawing Sheets

CHARGED PARTICLE BEAM IRRADIATION APPARATUS AND METHOD OF IRRADIATION WITH CHARGED PARTICLE BEAM

BACKGROUND OF THE INVENTION

1. Field of the Invention

The present invention relates to a charged particle beam irradiation apparatus and a method of irradiating an object with a charged particle beam. Further, the present invention relates to a therapeutic apparatus.

2. Discussion of Background

Figure 10:
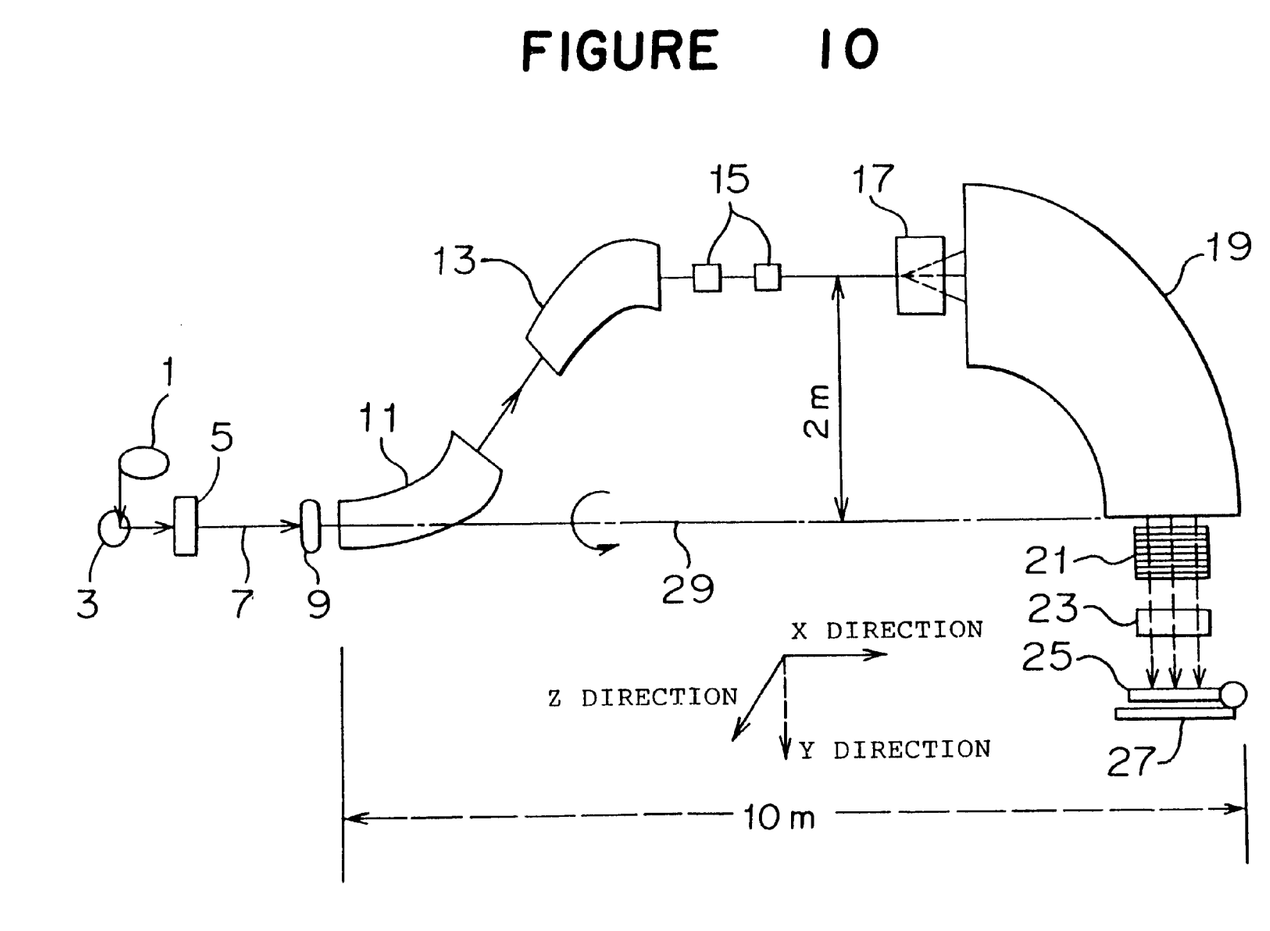
FIG. 10 is a block diagram showing an example of a conventional charged particle beam therapeutic apparatus.

FIG. 10 is a block diagram showing an example of a conventional therapeutic apparatus disclosed in "Medical Physics" 1995, vol. 22, p 37 by Pedroni et al. In the conventional therapeutic apparatus, a proton beam emitted from an accelerator 1 is carried by a transporting magnet 3, and is passed through an energy degrader 5 at the first stage, as an energy attenuating means in which a predetermined amount of energy is given to the proton beam. The proton beam is bent from the horizontal direction to an upward direction by a first deflection electromagnet 11, and is returned to the horizontal direction by a second deflection electromagnet 13. Further, the proton beam is converged by a converging electromagnet 15, and swept in a vertical direction by a scanning electromagnet 17. The swept proton beam is bent by a third (the last) deflection electromagnet 19 and passes in a just downward irradiate a patient 25 through a fine-adjusting energy degrader 21 and a dose-position monitor 23. The electromagnets 11, 13, 15, 17 and 19 are integrated with the energy degrader 21 and the monitor 23 so as to constitute an irradiation gantry. The irradiation gantry rotates around the rotating axis 29, and therefore, is called as a rotating gantry.

The proton beam irradiating to the patient 25 undergoes parallel scanning in only an X direction as shown in FIG. 10 by means of the scanning electromagnet 17 and the deflection electromagnet 19. The scanning of the proton beam in an Y axial direction, which is necessary for therapy, is effected by moving an irradiation bed 27. Scanning in a depth direction (a Z direction) is obtainable by adjusting the energy of the proton beam by means of the energy degrader 21.

In the above-mentioned conventional charged particle beam irradiation apparatus, parallel beam scanning in only a uniaxial direction (the X direction in the above-mentioned example) could be obtained, and it was necessary to move in the Y direction the patient 25 along with the bed 27 during therapy. The movement of the bed 27 might be uncomfortable to the patient, and at the same time, there may be an error of position in an irradiate area. Further, in the conventional apparatus, it was necessary to dispose the scanning electromagnet 17 at an upstream side of the deflection electromagnet 19 so as to obtain parallel beam scanning. Accordingly, the size of the deflection electromagnet 19 for deflecting the charged particle beam scanned by the scanning electromagnet 17 in the vertical direction, was increased, with the result that the total weight of the rotating gantry used for therapy was 100 tons or more. Further, the conventional apparatus had a problem with respect to the scanning in the depth direction with use of the energy degrader 21. Namely, the thickness of the energy degrader 21 was determined for each depth of scanning in a discontinuous manner, and beam irradiation was conducted in accordance with a predetermined distribution of irradiated particle number and depth so that a uniform dose of absorbed beam could irradiate a tumor. Accordingly, there was an influence of a shift of position in the irradiation area due to the breathing of the patient.

SUMMARY OF THE INVENTION

It is an object of the present invention to provide a charged particle beam irradiation apparatus and a method of irradiating a charged particle beam which can realize parallel scanning in a biaxial direction by the charged particle beam in a predetermined irradiation field without moving the bed and which can reduce the size and the weight of the rotating gantry.

Further, it is an object of the present invention to make the irradiation efficient and to minimize an error in determining the position of an irradiation area due to the breathing of a patient by effecting the scanning of the beam in a depth direction continuously, repeatedly and automatically.

In accordance with a first aspect of the present invention, there is provided a charged particle beam irradiation apparatus which comprises:

a scanning magnetic field generating means comprising two electromagnets which are arranged in series along the direction of an incident axis of a charged particle beam and which deflect the charged particle beam in opposite directions by a predetermined angle, an energy modulating means which comprises a cylindrical member having a predetermined length and a predetermined distribution of wall thickness in its circumferential direction, a means for rotating the cylindrical member around the rotation symmetric axis and a detecting means for detecting an angle of rotation of the cylindrical member, the energy modulating means being disposed at a downstream side of the scanning magnetic field generating means so that the deflected charged particle beam passes through the rotation symmetric axis, an energy attenuating means for limiting the maximum energy of the charged particle beam, and a means for rotating the scanning magnetic field generating means and the energy modulating means together around the incident axis of the charged particle beam.

In a second aspect of the present invention, there is provided a charged particle beam irradiation apparatus according to the first aspect wherein the predetermined angle of deflection of the charged particle beam by an upstream side electromagnet between the two electromagnets is the same as that by a downstream side electromagnet.

In a third aspect of the present invention, there is provided a charged particle beam irradiation apparatus according to the first aspect wherein the predetermined angle of deflection of the charged particle beam deflected by a downstream side electromagnet between the two electromagnets which are positioned in series is larger than that deflected by an upstream side electromagnet.

In a fourth aspect of the present invention, there is provided a method of irradiating a charged particle beam which comprises:

using the charged particle beam radiation apparatus described in the first aspect and employing the following steps to irradiate a predetermined three-dimensional irradiation area:

a first step of making the three-dimensional irradiation area approximated to a group of cylindrical columns arranged in parallel to the direction z of an incident charged particle beam with predetermined spaces wherein the coordinate Pi of the center of each cylindrical column in an XY direction is determined as the beam irradiation position; the length $\Delta zi$ of each cylindrical column is determined to be a scanning range in a beam propagating direction (a depth direction) at the beam irradiation position Pi, and the coordinate of the maximum depth of irradiation is to be zi, a second step of loading previously prepared parameters [(Pi, $\Delta zi$ and zi), i=1, 2, . . . N] for the irradiation area from a set table;

a third step of determining an angle of rotation and a strength of a magnetic field of the scanning magnetic field generating means and an angle of rotation of the energy modulating means in response to each Pi;

a fourth step of determining the maximum energy of the charged particle beam by an energy attenuating means in response to the maximum depth of irradiation zi; and a fifth step of determining an effective range of the angle of rotation based on data taken from the energy modulating means in response to the scanning range of depth $\Delta zi$ (initial value i=1), and irradiating the charged particle beam within the determined range.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Preferred embodiments of the present invention will be described in more detail with reference to the drawings wherein the same reference numerals designate the same or corresponding parts.

Embodiment 1

Figure 1:
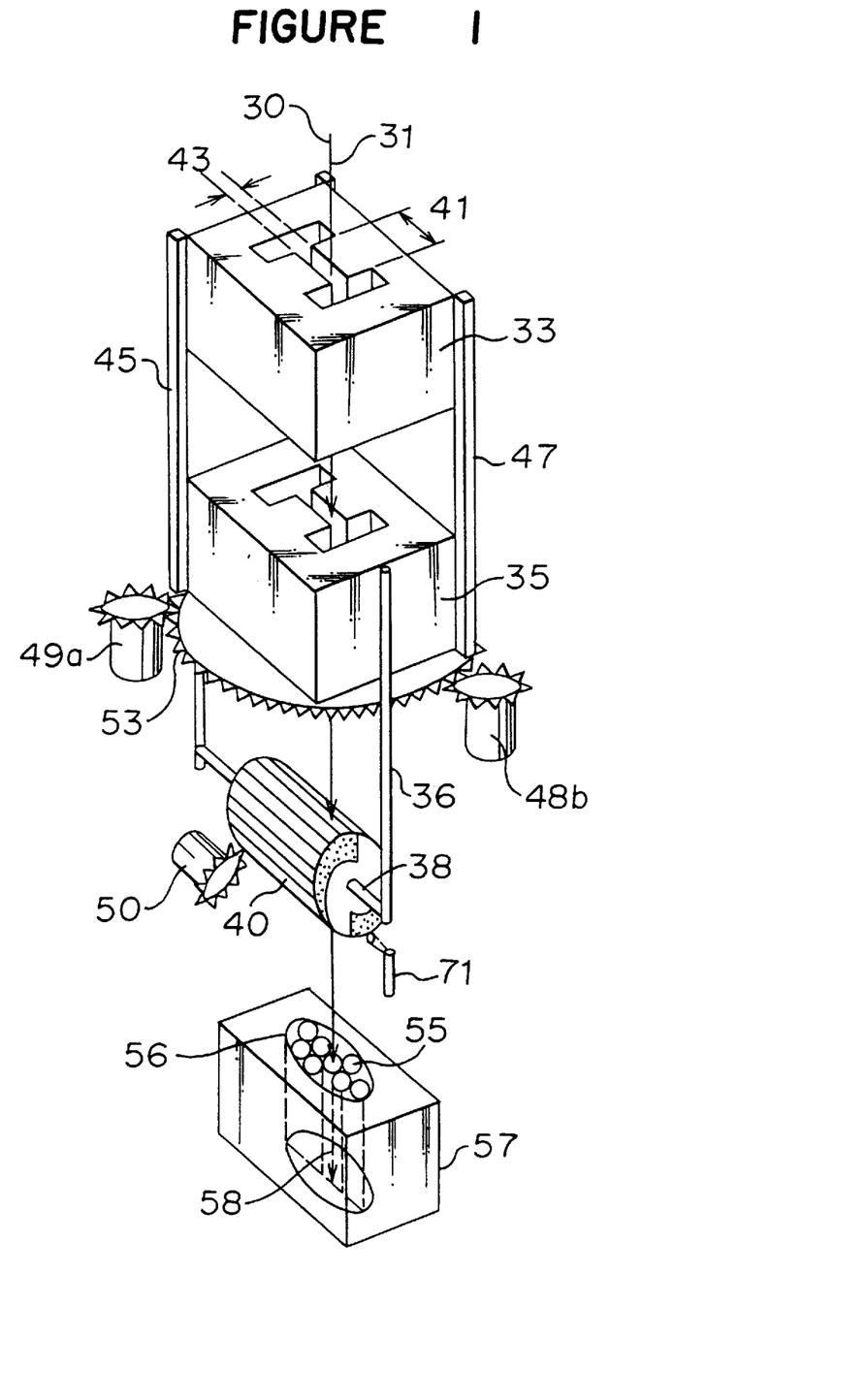
FIG. 1 is a block diagram showing a charged particle beam irradiation apparatus according to Embodiment 1 of the present invention.
Figure 2:
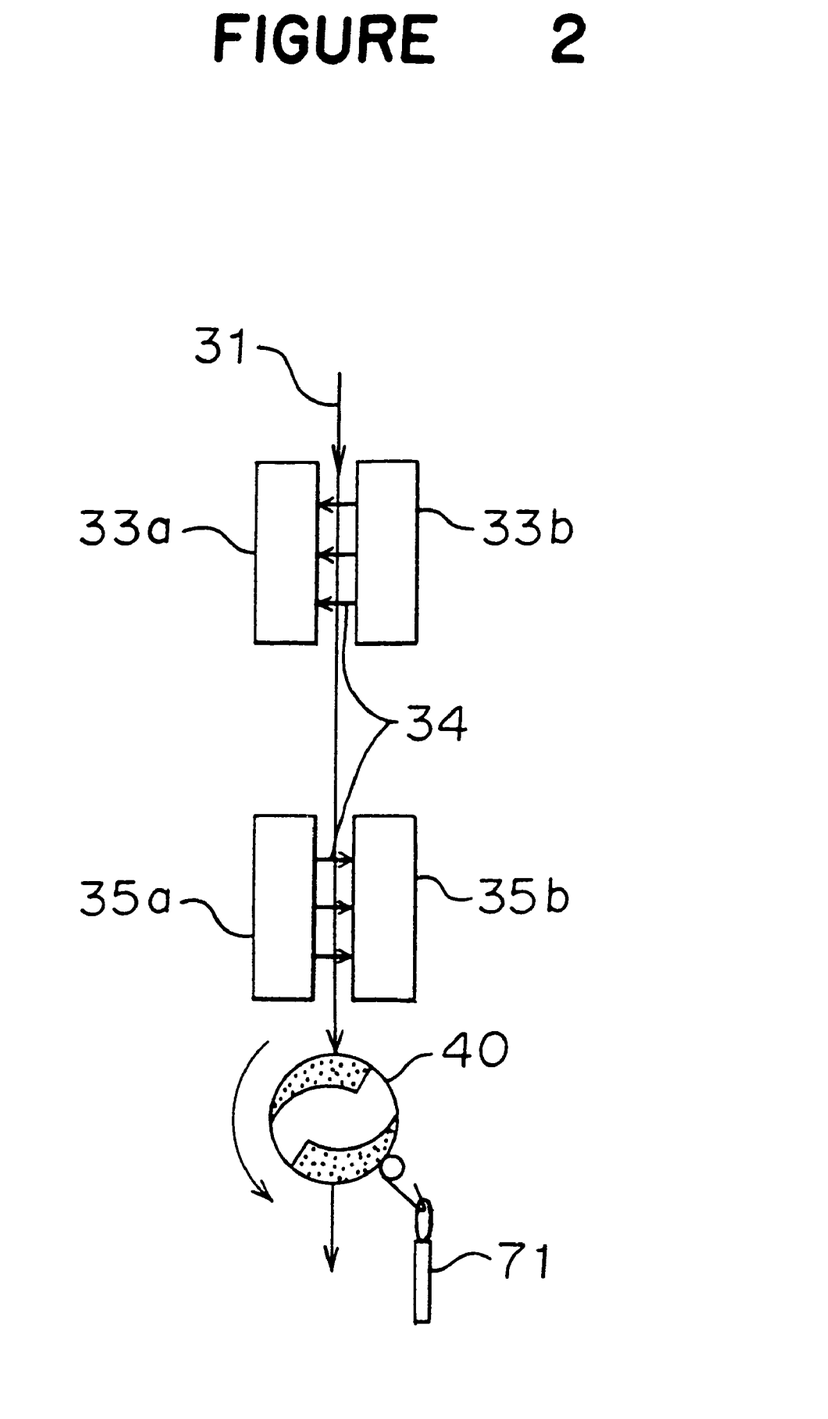
FIG. 2 is a block diagram showing a side view of electromagnets in the charged particle beam irradiation apparatus according to Embodiment 1 of the present invention.
Figure 3:
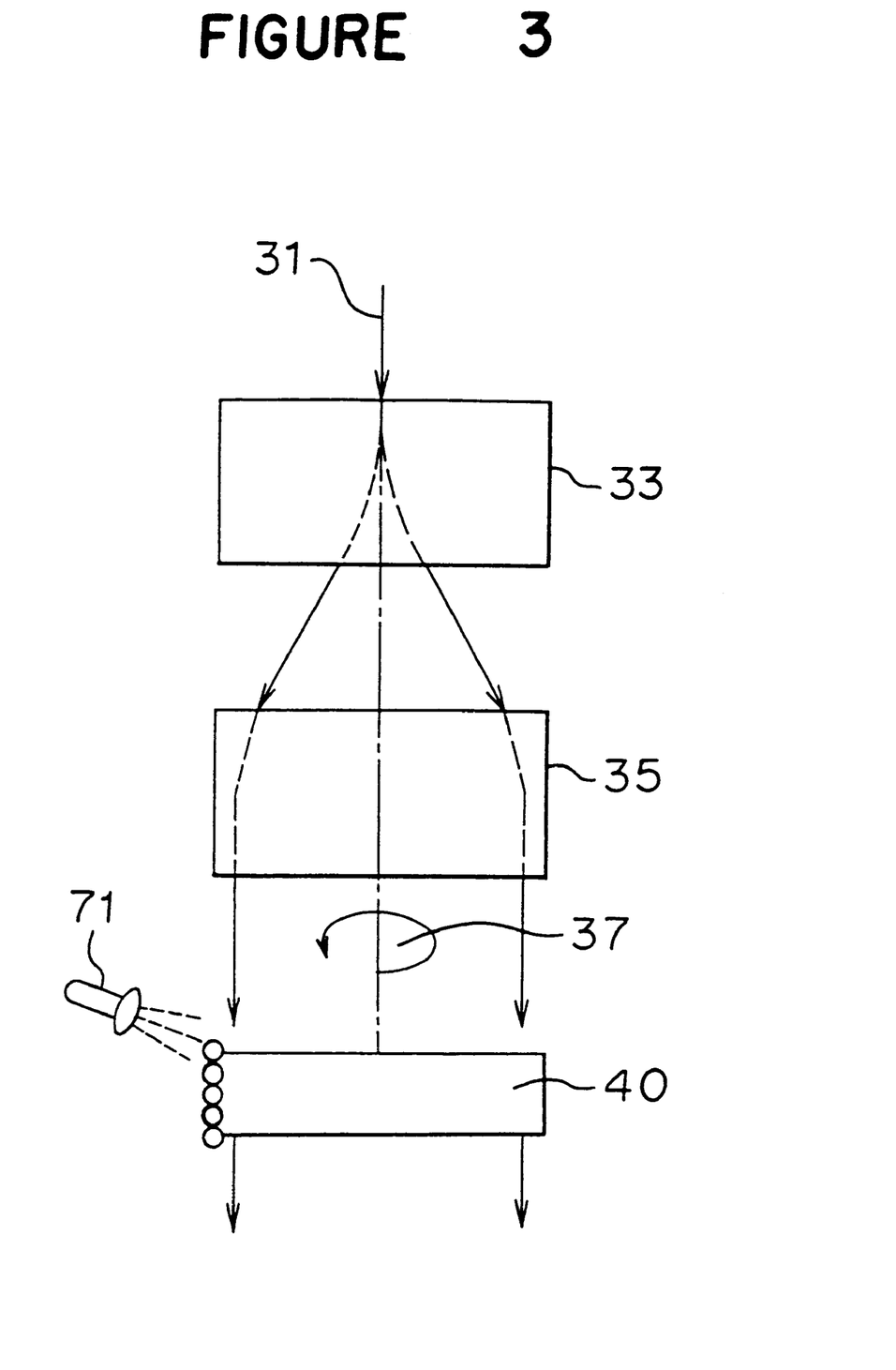
FIG. 3 is a diagram showing the electromagnets in the charged particle beam irradiation apparatus according to Embodiment 1 of the present invention, viewed from another angle.

Embodiment 1 of the present invention will be described with reference to FIG. 1, 2, 3, 7 and 9. In the drawings, reference numeral 30 designates an incident axis of a charged particle beam 31 (such as a proton beam, a carbon beam or the like). Two scanning electromagnets 33, 35 are disposed a predetermined distance apart from each other along the incident axis 30. The scanning electromagnets 33, 35 produce, respectively, a uniform magnetic field wherein the directions of the magnetic lines of force are opposite to each other and the strength and the length of the effective magnetic field (along the incident axis 30) is the same. Numeral 37 designates the rotating axis of the two scanning electromagnets 33, 35. Numeral 55 in FIG. 1 designates an example of the locus of a swept charged particle beam. Numeral 34 in FIG. 2 designates the directions of the magnetic fields produced by the electromagnets 33, 35. In FIG. 1, numeral 41 designates the magnetic pole width of the scanning electromagnets, numeral 43 designates the magnetic pole gap and numeral 53 designates a driving gear wheel for causing revolution. Numeral 40 designates an energy modulator which is proposed by Y. Jongen et al. in "Proceeding of the NIRS International Workshop on Heavy Charged Particle Therapy and Related Subjects, July 1991, Chiba, Japan, ed. A. Itano and T. Kanai (1991), pp. 189–200" and which changes periodically the energy of the charged particle beam scanned by the scanning electromagnets 33, 35 according to a predetermined distribution within a range corresponding to a range shown by numeral 75 in FIG. 7, which indicates a scanning range $\Delta zi$ in a depth direction at an irradiation position Pi. In the present invention, the energy modulator 40 having a cylindrical shape is firmly connected with the two scanning electromagnets 33, 35. Accordingly, scanning in a depth direction can be conducted by the energy modulator 40, which is at a fixed position, irrespective of the scanning positions of the scanning electromagnets 33, 35. The energy modulator 40 is driven by a motor 50 and rotated around its rotating axis 38. The electromagnets 33, 35 are firmly connected by means of connecting frames 45, 47, and a pair of supporting rods support the rotating axis 38 of the energy modulator 40 so that the energy modulator 40, the scanning electromagnets 33, 35 and the motor 50 are formed integrally. Numerals 48b and 49a designate motors each having a gear wheel meshed with the gear wheel 53 so that the scanning electromagnets 33, 35 are rotated. The charged particle beam scanned by the scanning electromagnets 33, 35 always pass through a plane including the rotating axis 38 of the energy modulator 40 irrespective of an angle of rotation and a strength of the magnetic field of the scanning electromagnets 33, 35.

Figure 7:
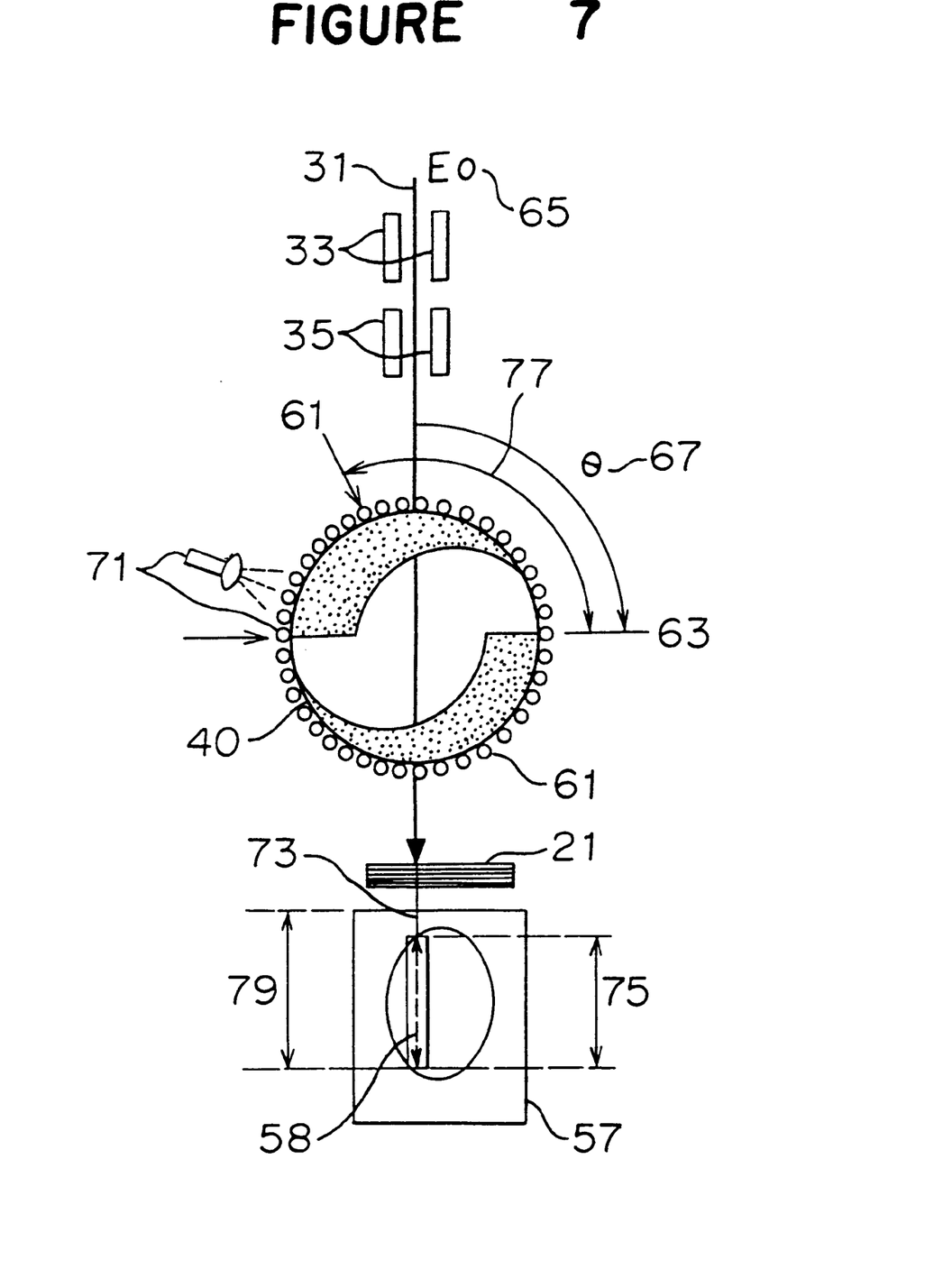
FIG. 7 is a block diagram showing the principle of the charged particle beam therapeutic apparatus according to the present invention.

Numeral 71 designates a detecting means for detecting an angle of rotation of the energy modulator 40 by means of an optical encoder. Accordingly, the charged particle beam can periodically be irradiated only within an optional angular range of the energy modulator.

Numeral 65 in FIG. 7 indicates an energy E0 of the charged particle beam scanned by the scanning electromagnets 33, 35. Numeral 61 designates a beam irradiation stopping position and numeral 63 designates a beam irradiation starting position among marks indicating positions which are marked on the energy modulator 40. The beam irradiation starting position 63 is fixed and the beam irradiation stopping position 61 is determined depending on a required scanning length $\Delta zi$ (75) in a depth direction. The maximum depth zi (79) which the charged particle beam can reach can be determined by adjusting the reduction $\Delta Ei$ of the energy by means of the energy degrader 21 (energy attenuating means). The energy degrader 21 is a single energy absorbing plate or laminated energy absorbing plates. The energy degrader 21 may be constituted by two opposing wedge-like energy absorbing plates wherein the sum of the thickness of the two energy absorbing plates is changed in a short time by moving them relative to each other. In FIG. 7, numeral 67 indicates an angle of rotation $\theta$ of the energy modulator 40. A position indicated by $\theta=0$ or 180 corresponds to the beam irradiation starting position 63.

Explanation will be made as to the operation of the charged particle beam irradiation apparatus according to Embodiment 1 of the present invention with use of FIGS. 1, 2, 3, 7 and 9.

In FIG. 7, the charged particle beam 31 emitted with a predetermined beam energy E0 (65) is bent by a predetermined angle by the scanning electromagnet 33, and is bent by the same angle in the opposite direction by the scanning electromagnet 35 which produces a magnetic field in the opposite direction wherein the strength and length of magnetic field are the same as the scanning electromagnet 33. Then, the charged particle beam 31 is passed through the energy modulator 40 and the energy degrader 21 and transformed into a beam parallel to the original charged particle beam 31, which irradiates an irradiated object 57. In this case, the energy of the charged particle beam irradiating to an irradiation area is periodically changed according to a range and a distribution function, which are determined by a distribution of wall thickness along the circumferential direction of the energy modulator 40, with the continuous rotation of the energy modulator 40. Accordingly, repeated scanning to a predetermined depth $\Delta zi$ (75) can automatically be carried out to the irradiated object in its depth direction as shown by a locus of sweeping 58 in FIG. 1 or 7.

Further, since the electromagnets 33, 35 and the energy modulator 40 are formed integrally by means of the connecting frames 45, 47 and the supporting rods 36 as shown in FIG. 1, a three-dimensional irradiation pattern which is represented by numeral 56 can be realized in the irradiated object 57 when the one-piece body of the electromagnets 33, 35 and the energy modulator 40 is rotated around the rotating axis 37 by means of a rotating means such as the motors 49a, 49b. Thus, the scanning in the depth direction (the z direction) by the energy modulator 40 is carried out at the beginning, and the scanning in XY directions is dispersively carried out later, which is effected by the rotation and a change of the strength of the magnetic fields in the scanning electromagnets 33, 35. However, the order of the scanning may be reversed.

Figure 9:
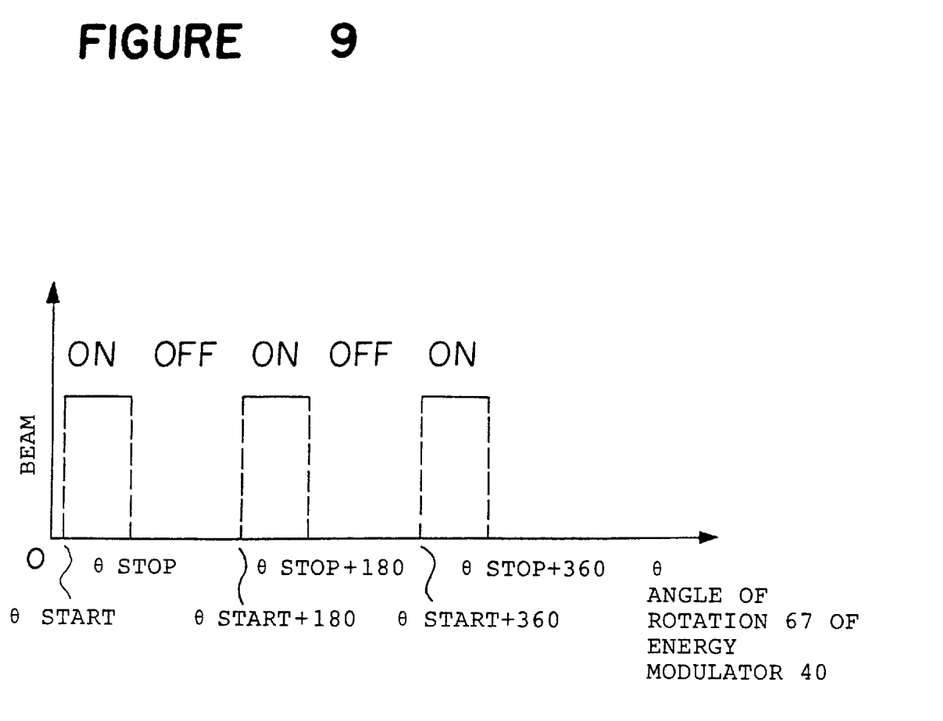
FIG. 9 is a diagram showing the principle of ON/OFF control to the charged particle beam in Embodiments 1 to 4 of the present invention in response to angles of the energy modulator 40.

In FIG. 7, the detecting means 71 for detecting an angle of rotation of the energy modulator 40 detects the irradiation starting position 63 and the irradiation stopping position 61 whereby ON/OFF control of the charged particle beam 31 is conducted in association with a beam stopper for repeated irradiation as shown in FIG. 9. In FIG. 7, numeral 73 designates a coordinate of a position Pi in the irradiated area in a plan view; numeral 75 designates a length of scanning $\Delta zi$ in a depth direction at the coordinate of the position Pi; numeral 79 designates the maximum depth zi of scanning in the depth direction at the coordinate of the position Pi. The maximum depth of scanning zi (79) at every coordinate of the position Pi can be set with the energy degrader 21, and the length of the scanning $\Delta zi$ (75) in the depth direction can be adjusted by suitably determining the-irradiation stopping position 61. Accordingly, a scanning pattern or a distribution of the number of charged particles in the depth direction is determined by a distribution of the wall thickness in the circumferential direction of the energy modulator 40 regardless of the magnitudes of $\Delta zi$ (75) and zi (79). The corresponding range of the distribution is determined by a range of scanning angle $\Delta\theta i$ (77) shown in FIG. 7. When the charged particle irradiation apparatus according to Embodiment 1 is applied to a charged particle beam therapeutic apparatus, a uniform dose can be applied to a tumor having a complicated shape.

In Embodiment 1, the scanning electromagnets 33, 35 having the same strength of the magnetic field and the same length of the effective magnetic field are used. However, the strength and the length need not always be the same as long as the charged particle beam 31 can be bent at the same angle in opposite directions. Further, in Embodiment 1, the two scanning electromagnets 33, 35 are used so that the charged particle beam 31 is scanned parallel to the incident axis 30. However, any device which can produce magnetic fields for scanning such as a single or a plurality of electromagnets or permanent magnets contrived to produce magnetic fields for scanning (for example, an arrangement of permanent magnets being spatially changed mechanically) can be used as long as it can produce two magnetic fields for scanning which deflect the charged particle beam 31 by an identical angle in opposite directions.

In the Embodiment of the present invention, the scanning by the parallel beams in a biaxial direction can be made compact, and the magnetic pole gaps 43 of the scanning electromagnets 33, 35 can be reduced to around the size in cross section of the incident charged particle beam 31, whereby the size and the weight of the irradiation apparatus can be remarkably reduced.

Further, in the charged particle beam therapeutic apparatus employing the charged particle beam irradiation apparatus of the present invention, means for realizing efficiently the scanning by the beam in the depth direction can be provided. Also, since the scanning is conducted automatically and repeatedly on the same irradiation area, an error of irradiation of an internal organ of a patient due to a variation of position in its depth (z) direction can be reduced. Further, with the combination of the energy modulator 40 of cylindrical form and the above-mentioned compact charged particle beam scanner, a charged particle beam therapeutic apparatus of simple structure which achieves the above-mentioned effect efficiently can be realized.

Embodiment 2

Figure 4:
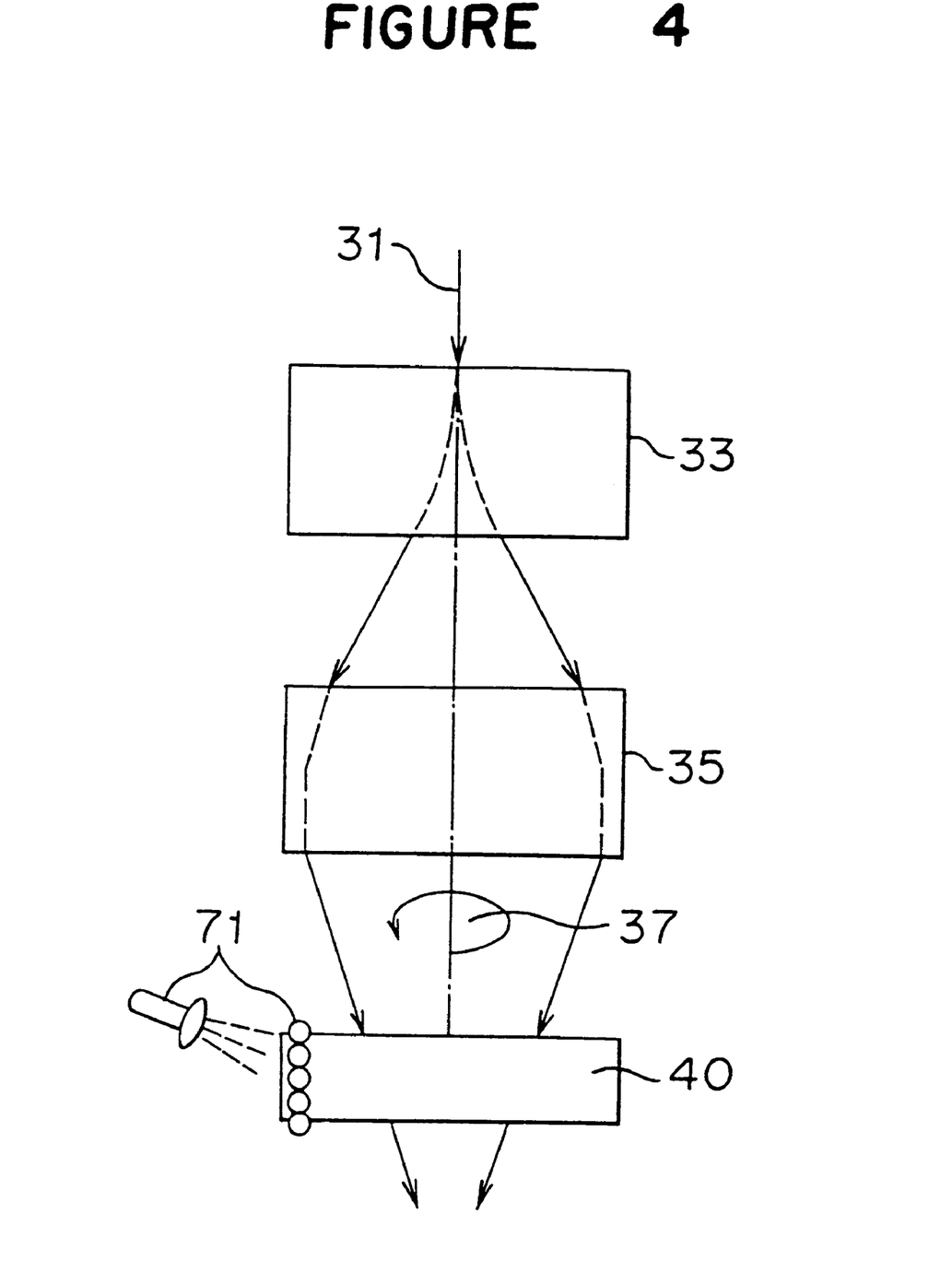
FIG. 4 is a diagram showing scanning electromagnets in the charged particle beam irradiation apparatus according to Embodiment 2 of the present invention.

FIG. 4 is a diagram showing scanning electromagnets for the charged particle beam irradiation apparatus according to Embodiment 2 of the present invention. In FIG. 4, numeral 31 designates a charged particle beam, numerals 33, 35 designate the same scanning electromagnets as used in Embodiment 1, numeral 37 designates the rotating axis of the scanning electromagnets, and numeral 40 designates the energy modulator as described in Embodiment 1. The charged particle beam irradiation apparatus according to Embodiment 2 is the same as that in Embodiment 1 except that design of the scanning electromagnets 33, 35 is so made that a beam deflection angle of the scanning electromagnet 33 is different from a beam deflection angle of the scanning electromagnet 35 whereby the charged particle beam 31 is converged for scanning the irradiated object at a predetermined angle.

In the same manner as in Embodiment 1, the charged particle beam irradiation apparatus according to Embodiment 2 can realize a compact structure for converged charged particle beam scanning in a two-dimensional direction by rotating the one-piece body comprising the scanning electromagnets 33, 35 and the energy modulator 40 around the rotating axis 37.

The charged particle beam irradiation apparatus of this embodiment, when applied to a charged particle beam therapeutic apparatus for curing a tumor at a deep position, can reduce an irradiation dose of the skin of a patient. Further, the present invention can provide a compact two-dimensional converged charged particle beam scanning apparatus.

Description has been made as to Embodiment 2 wherein the energy modulator 40 is employed. However, the present invention can realize three-dimensional converged charged particle beam scanning as described before, by using the energy degrader 21 (as shown in FIG. 7) as a simple energy changing means, without using the energy modulator 40.

Embodiment 3

Figure 5:
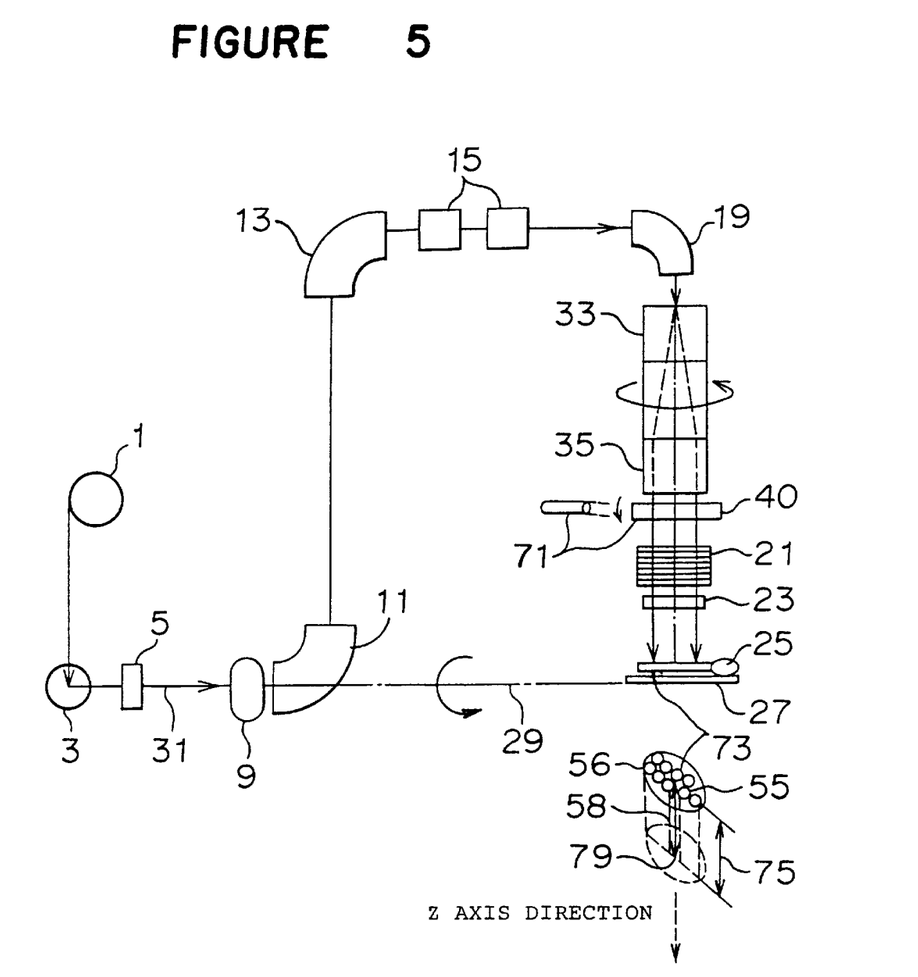
FIG. 5 is a block diagram showing a charged particle beam therapeutic apparatus according to Embodiment 3 of the present invention.

FIG. 5 is a block diagram showing a charged particle beam therapeutic apparatus according to Embodiment 3 of the present invention. In FIG. 5, reference numeral 31 designates a charged particle beam, numerals 33, 35 designate the same scanning electromagnets as used in Embodiment 1, numeral 40 designates the same energy modulator as used in Embodiment 1, numeral 37 designates the rotating axis of a one-piece body comprising the scanning electromagnets 33, 35 and the energy modulator 40, and numeral 55 designates a locus of a swept charged particle beam. The other reference numerals designate the same elements as those in FIGS. 1, 2, 3 and 7 as in well as FIG. 10 showing a conventional example.

Figure 6:
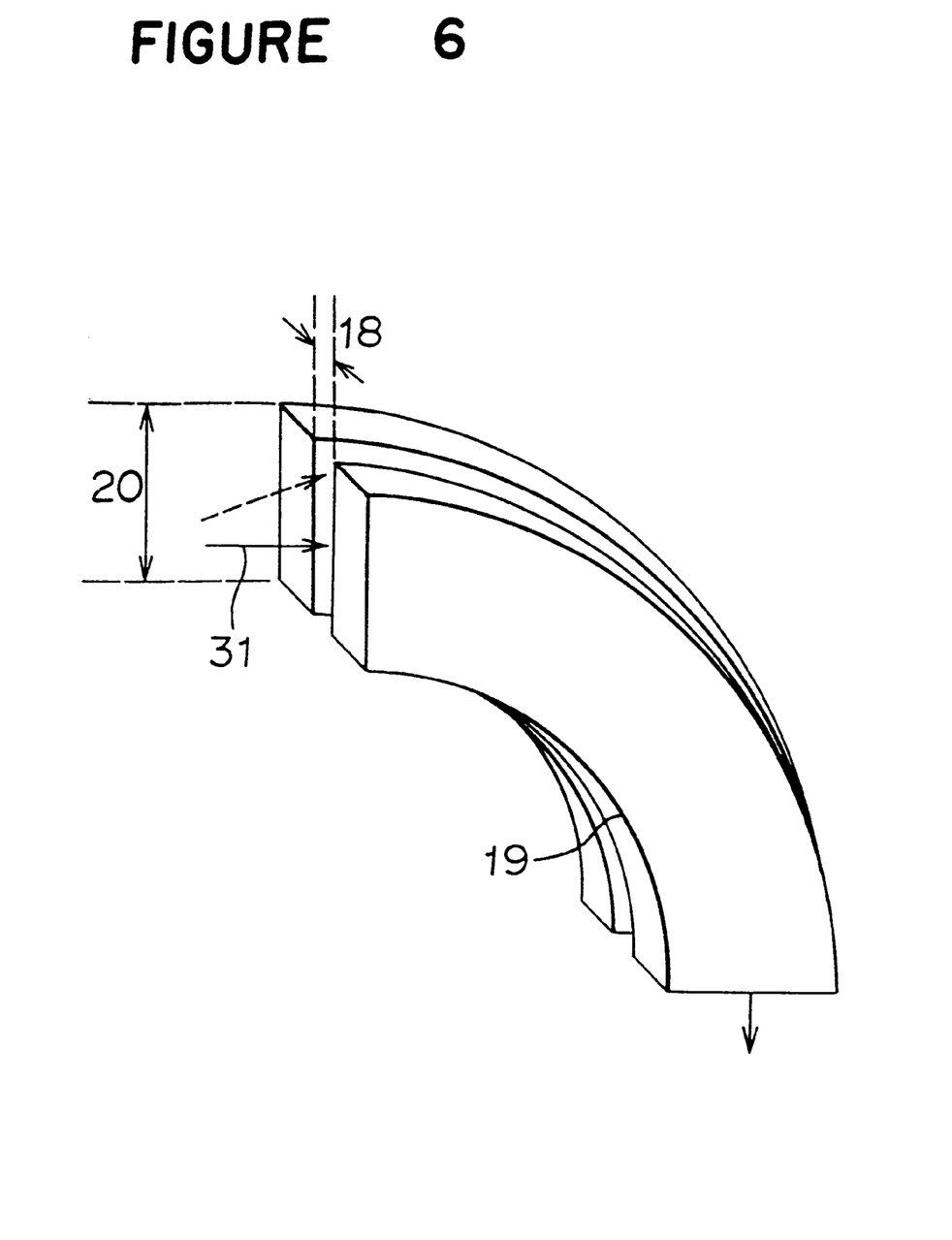
FIG. 6 is a block diagram showing a deflection electromagnet in the charged particle beam therapeutic apparatus according to Embodiment 3 of the present invention.

The charged particle beam therapeutic apparatus according to Embodiment 3 of the present invention will be described with reference to FIGS. 5, 6, 7 and 9 wherein the same reference numerals designate the same or corresponding parts. In the charged particle beam therapeutic apparatus constructed as shown in the Figures, a charged particle beam of high energy emitted from an accelerator 1 is carried by a transporting electromagnet 3 and passed through an energy degrader 5 at the first stage where the beam is transformed into a charged particle beam 31 having a predetermined energy. The charged particle beam 31 is returned from a horizontal direction to an upward direction by a first deflection electromagnet 11 and is again returned to the horizontal direction by a second deflection electromagnet 13. A beam stopper 9 limits irradiation time by turning on and turning off the charged particle beam 31 whereby a beam irradiation area is restricted in synchronism with the beam scanning. The charged particle beam is converged by converging electromagnets 15 before entering into a third deflection electromagnet 19. In the third embodiment, unlike the conventional technique as shown in FIG. 10, the beam scanning is not conducted before the third deflection electromagnet 19 and the charged particle beam is bent while maintaining a thin pencil-like form to just below the third deflection electromagnet 19. Accordingly, both the magnetic pole width 20 and the magnetic pole gap 18 of the deflection electromagnet 19 (as shown in FIG. 6) can be made small, and hence, the total weight of the rotating gantry can be reduced. On the other hand, in the conventional apparatus as shown in FIG. 10, the magnetic pole width 20 of the third deflection electromagnet 19 had to cover the area of the charged particle beam scanned by the scanning electromagnet 17. In fact, the magnetic pole width 20 reached several tens of cm in size.

The charged particle beam emitted through the third deflection electromagnet 19 is passed through the scanning electromagnets 33, 35, the energy modulator 40 and the energy degrader 21 to scan a three-dimensional area in the irradiated object 57 in the same manner as explained in Embodiment 1. With respect to the scanning in a depth direction, the thickness of the energy degrader 21 is set so that the scanning of the maximum depth can be performed. Then, an angular range for the operation of the energy modulator 40 is determined as follows. An angular position corresponding to the starting of the emission of the charged particle beam is fixed to the irradiation starting position 63 on the energy modulator 40, and an angular position corresponding to the stopping of the charged particle beam is determined to be the irradiation stopping position 61 so as to meet the length Δzi (75) in the depth direction for the scanning required, as shown in FIG. 7. Within the determined range, the irradiation of the charged particle beam is conducted as shown in FIG. 9. In this case, even when the length Δzi (75) in the depth direction for the required scanning is different at every irradiation point Pi (73), which is determined by an angle of rotation of the scanning electromagnets 33, 35 and the strength of the magnetic fields of the electromagnets 33, 35, a predetermined distribution of charged particles or a predetermined distribution of an absorbed dose, which is determined depending on a distribution of the wall thickness of the energy modulator 40, can be provided to the irradiated object in its depth direction. Specifically, a distribution of the wall thickness in its circumferential direction of the energy modulator 40 is determined so as to give to a tumor volume a uniform distribution of absorbed dose, as described in the above-mentioned paper issued by Y. Jongen et al.

A charged particle beam therapeutic apparatus may require a uniform distribution of charged particles in a depth direction or a uniform distribution of absorbed dose at every irradiation point. In this case, in comparison with the scanning in the depth direction with only the energy degrader 21 as described with respect to the conventional example, the present invention can increase efficiency of scanning, and can irradiate to an irradiated object placed in a stationary state, whereby an error of irradiation due to a positional change of the object can be controlled.

In this embodiment, since the parallel beam scanning can be obtained in a biaxial direction as shown in FIG. 5, the movement of the bed 27 on which a patient 25 is placed becomes unnecessary, and therefore, accuracy of irradiating position in the therapeutic apparatus can be improved. When a proton beam having an energy position of 250 MeV (the rigidity (the amount of action of a magnetic field required for bending the beam by 1 radian; equivalent to a radius of gyration in a magnetic field of 1 tesla) is 2.43 tesla·m), required for curing a tumor at a deep position, is used as the charged particle beam, and the scanning is effected to an irradiation area 20 cm in diameter, the size of the third deflection electromagnet 19 can be reduced to about 40 cm provided that the electromagnet is made superconductive. Further, since the length from one end to the other end of the scanning electromagnets 33, 35 can be about 120 cm, the radius of gyration of the rotating gantry can be suppressed to about 2 m. Thus, according to the present invention, unlike the conventional apparatus as shown in FIG. 10, the patient 25 can be placed on the center axis of rotation of the rotating gantry while two dimensional parallel beam scanning can be realized. Thus, the structure of the rotating gantry can be remarkably simplified. Further, in this embodiment, it is possible to reduce the weight of the rotating gantry therapeutic apparatus for emitting a proton beam of 250 MeV to half or less in comparison with that of the conventional apparatus shown in FIG. 10. Further, the embodiment of the present invention, when applied to charged particle beam therapy, can provide the effect as described in Embodiment 1.

Embodiment 4

Figure 8:
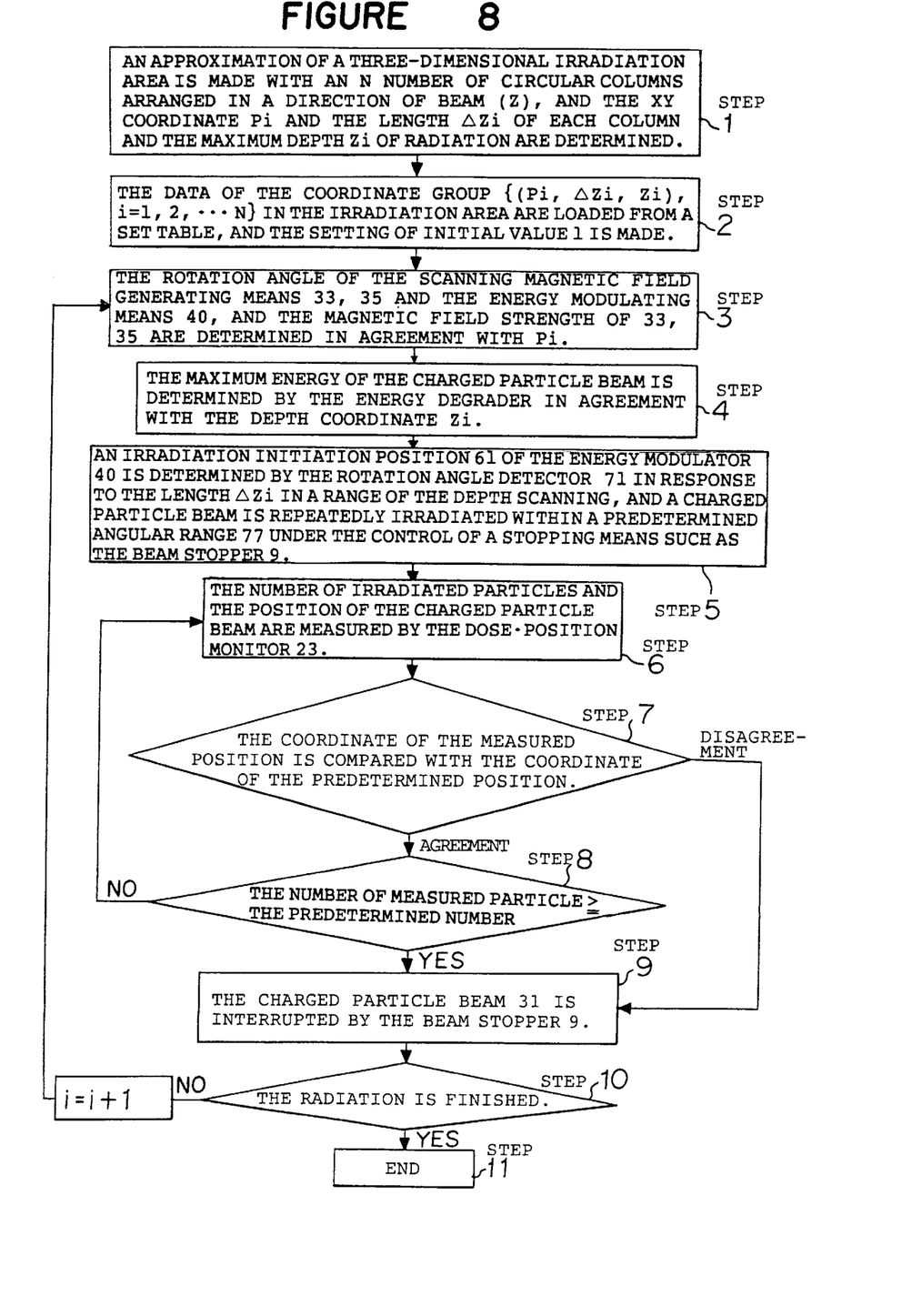
FIG. 8 is a flow chart showing a method of irradiation with a charged particle beam according to Embodiment 4 of the present invention.

FIG. 8 is a flow chart showing a method of irradiating a charged particle beam according to Embodiment 4 of the present invention. Description will be made as to Embodiment 4 concerning the irradiation method with reference to FIG. 8 as well as FIG. 5 concerning Embodiment 3 and FIGS. 7 and 9 concerning Embodiment 1.

Step 1: in FIG. 7, a three-dimensional irradiation area is approximated to a group of cylindrical columns arranged in parallel to the charged particle beam incident axis 30, with predetermined spaces, wherein the coordinate Pi (73) of each cylindrical column in an XY plane (which is perpendicular to the direction of irradiation) is determined to be the position of irradiation; the length $\Delta z_i$ (75) of each cylindrical column is determined to be a scanning range in a beam propagating direction (a depth direction) at the beam irradiation position Pi (75), and the coordinate of the maximum depth of irradiation is to be $z_i$ (79) where i is an integer from 1 to N, and N is the number of cylindrical columns for defining the three-dimensional irradiation area.

Step 2: previously prepared parameters [(Pi, $\Delta z_i$, $z_i$), i=1, 2, ... N] of the three-dimensional irradiation area are loaded into a control means such as a computer for controlling the irradiation apparatus from a set table.

Step 3: an angle of rotation and a strength of the magnetic field of the scanning electromagnets 33, 35, and an angle of rotation of the energy modulator 40 are determined in response to the coordinates Pi in the XY plane (i=1 as the initial value).

Step 4: the maximum energy of the charged particle beam 31 is determined by the energy degrader 21 in response to the maximum depth of irradiation $z_i$ (i=1 as the initial value).

Step 5: an effective range of an angle of rotation of the energy modulator 40 is determined in response to the scanning range of depth $\Delta z_i$ (i=1 as the initial value), and the charged particle beam irradiates only within the effective range under the control of the beam stopper 9 as a beam stopping means.

Step 6: the number of charged particles and the position of the incident charged particle beam are measured by the position dose monitor 23.

Step 7: the coordinate measured at Step 6 is compared with the coordinate measured at Step 3. When there is no agreement, the operation is moved to Step 9.

Step 8: when the measured coordinate is in agreement with the set coordinate as the result of comparison at Step 7, a determination is made whether or not an accumulated value of the number of particles measured at Step 6 exceeds a predetermined number of particles at each of the coordinates Pi which have previously been determined before the initiation of the irradiation. When the accumulated value does not exceed the predetermined number, the operation is returned to Step 6.

Step 9: when the result of the comparison at Step 8 is YES, the irradiation by the charged particle beam 31 is stopped by means of the beam stopper 9.

Step 10: a determination is made whether or not the irradiation is finished. When the irradiation is to be continued, a numerical value of 1 is added for i, and then, the operation is returned to Step 3.

Step 11: the irradiation is finished.

In the manner as described above, the operations from Step 3 to step 11 are executed for i=1 through N whereby predetermined numbers of charged particles [Ni, i=1, 2, ... N] are irradiate to all the cylindrical columns in the three-dimensional irradiation area defined by the coordinates [(Pi, $\Delta z_i$, $z_i$), i=1, 2, ... N].

FIG. 9 is a diagram showing a relation of the rotation of the energy modulator 40 to ON/OFF control by the beam stopper over time. In the control method shown in FIG. 9, it is sufficient to continuously rotate the energy modulator 40 at a constant speed. When the lowest position of the length of the beam scanning $\Delta z_i$ is in agreement with the maximum depth $z_i$, the position of "θ start" in FIG. 9 may be zero.

In the above-mentioned operations, the same effect is obtainable even when the order of Step 3 is replaced by Step 4.

Further, in the above-mentioned method, since the revolution rate of the scanning electromagnets 33, 35 is smaller than the scanning rate with a strength of the magnetic fields, irradiation time can be shortened by scanning first with the magnetic fields while the angle of rotation of the scanning electromagnets is kept constant.

The present invention is applicable not only to the above-mentioned apparatus, method and charged particle therapy but also to a semiconductor and materials processing and so on in which the irradiation for the implantation of a charged particle beam is necessary.

In accordance with the first aspect of the present invention, the charged particle beam can be irradiated to an optional three-dimensional irradiation area while an irradiated object is kept still. Further, the size and the weight of the particle beam irradiation apparatus of the present invention can be reduced.

According to the second-aspect of the present invention, the charged particle beam can be irradiated in parallel into an optional three-dimensional irradiation area while an irradiated object is kept still.

According to the third aspect of the present invention wherein a predetermined angle of deflection of the charged particle beam deflected by a downstream side electromagnet between two electromagnets which are positioned in series is larger than that deflected by an upstream side electromagnet, the charged particle beam can be converged for irradiation to an optional three-dimensional irradiation area while an irradiated object is kept still. Further, when the third aspect of the invention is applied to therapy, a dose of irradiation to a normal texture other than the irradiation area can be reduced.

According to the fourth aspect of the present invention, the charged particle beam can correctly and efficiently be irradiated to an optional three-dimensional irradiation area while an irradiated object is kept still.

Obviously, numerous modifications and variations of the present invention are possible in light of the above teachings. It is therefore to be understood that within the scope of the appended claims, the invention may be practiced otherwise than as specifically described herein.

What is claimed is:

1. A charged particle beam irradiation apparatus comprising:
    scanning magnetic field generating means comprising two electromagnets arranged in series along a direction of an incident axis of a charged particle beam and deflecting the charged particle beam in opposite directions,
    energy modulating means comprising a cylindrical member having a length and a distribution of wall thickness in a circumferential direction, means for rotating the cylindrical member around a rotation axis, and detecting means for detecting angle of rotation of the cylindrical member, the energy modulating means being disposed at a downstream side of the scanning magnetic field generating means so that the charged particle beam passes through the rotation axis, energy attenuating means for limiting energy of the charged particle beam, and means for rotating the scanning magnetic field generating means and the energy modulating means together around the incident axis of the charged particle beam.

2. The charged particle beam irradiation apparatus according to claim 1, wherein the angle of deflection of the charged particle beam by an upstream side electromagnet of the two electromagnets is equal to an angle of deflection of a downstream side electromagnet of the two electromagnets.

3. The charged particle beam irradiation apparatus according to claim 1, wherein the angle of deflection of the charged particle beam deflected by a downstream side electromagnet of the two electromagnets is larger than an angle of deflection by an upstream side electromagnetic of the two electromagnets.

4. The charged particle beam irradiation apparatus according to claim 1, including a beam stopper cooperating with the detecting means for detecting an angle of rotation of the energy modulating means for ON/OFF control of the charged particle beam.

5. A method of irradiation with a charged particle beam with a charged particle beam irradiation apparatus comprising:

scanning magnetic field generating means comprising two electromagnets arranged in series along a direction of an incident axis of a charged particle beam and deflecting the charged particle beam in opposite directions, energy modulating means comprising a cylindrical member having a length and a distribution of wall thickness in a circumferential direction, means for rotating the cylindrical member around a rotation axis, and detecting means for detecting angle of rotation of the cylindrical member, the energy modulating means being disposed at a downstream side of the scanning magnetic field generating means so that the charged particle beam passes through the rotation axis, energy attenuating means for limiting energy of the charged particle beam, and means for rotating the scanning magnetic field generating means and the energy modulating means together around the incident axis of the charged particle beam, the method comprising irradiating a three-dimensional irradiation area by:

approximating the three-dimensional irradiation area as a group of cylindrical columns arranged parallel to an incidence direction z of an incident charged particle beam wherein a coordinate $P_i$ of the center of each cylindrical column in an XY direction is the beam irradiation position, a length $\Delta z_i$ of each cylindrical column is a scanning range in a beam propagating direction (a depth direction) at the beam irradiation position $P_i$, and the coordinate of the maximum depth of irradiation is $z_i$;

loading as previously prepared parameters $P_i$, $\Delta z_i$ and $z_i$, and $i=1, 2, \ldots N$ for the irradiation area from a set table;

determining an angle of rotation and a strength of a magnetic field of the scanning magnetic field generating means and an angle of rotation of the energy modulating means in response to each $P_i$;

determining the maximum energy of the charged particle beam with the energy attenuating means in response to the maximum depth of irradiation $z_i$; and determining an effective range of the angle of rotation based on data from the energy modulating means in response to the scanning range of depth $\Delta z_i$ (initial value i=1), and irradiating with the charged particle beam within the effective range.

6. The method of irradiating a charged particle beam according to claim 5, comprising measuring the number of charged particles in the irradiating charged particle beam and the position of the charged particle beam.

7. The method of irradiating a charged particle beam according to claim 5, comprising continuing irradiation with the charged particle beam until the number of the charged particles reaches a predetermined value.

* * * * *